United States Patent [19]

Preusser et al.

[11] 4,081,355
[45] Mar. 28, 1978

[54] PROCESS FOR RECOVERING HIGHLY PURE AROMATICS FROM A MIXTURE OF AROMATICS AND NON-AROMATICS

[75] Inventors: Gerhard Preusser, Essen; Martin Schulze, Neviges; Klaus Richter; Wilhelm Huwels, both of Essen, all of Germany

[73] Assignee: Krupp-Koppers GmbH, Essen, Germany

[21] Appl. No.: 736,151

[22] Filed: Oct. 27, 1976

Related U.S. Application Data

[63] Continuation of Ser. No. 526,367, Nov. 22, 1974, abandoned, which is a continuation of Ser. No. 432,341, Jan. 10, 1976, abandoned, and Ser. No. 170,900, Aug. 11, 1971, abandoned.

[30] Foreign Application Priority Data

Aug. 12, 1970 Germany .................. 2040025

[51] Int. Cl.$^2$ .................. B01D 3/40; C10G 7/00
[52] U.S. Cl. .................. 208/313; 203/39; 203/58; 203/63; 208/316; 208/321; 208/322; 208/326; 208/330; 208/334; 260/674 SE
[58] Field of Search .................. 203/53, 57, 58, 39, 203/42, 45, 46, 63, 91, 92, 95; 260/674 SE, 674 R; 208/326, 308, 311, 313–316, 321, 322, 325, 330, 333, 334

[56] References Cited

U.S. PATENT DOCUMENTS

| | | | |
|---|---|---|---|
| 3,262,875 | 7/1966 | Girotti et al. | 208/326 |
| 3,537,984 | 11/1970 | Thompson | 260/674 SE |
| 3,720,605 | 3/1973 | Paret et al. | 208/326 |
| 3,721,620 | 3/1973 | Paret et al. | 208/326 |

Primary Examiner—Frank Sever
Attorney, Agent, or Firm—Michael J. Striker

[57] ABSTRACT

Process for recovering highly pure aromatic substances from mixtures of hydrocarbons which contain in addition to the aromatic substances, large amounts of non-aromatic substances by liquid-liquid extraction in combination with an after arranged extractive distillation whereby the liquid-liquid extraction of the starting hydrocarbon mixture is carried out under such conditions that the resulting extract contains substantially the total amount of the aromatic substances and a portion of the non-aromatic substances, introducing this extract into an after arranged extractive distillation for further separating said extract whereby the sump product (extract phase) formed is drawn off and introduced into an after arranged distillation column where it is separated into an aromatic and a solvent fraction, while the head product of the extractive distillation (raffinate phase) is reintroduced into the bottom of the extractor for liquid-liquid extraction thereof, wherein there is used in both of the extracting stages, as selective solvent, morpholine and/or N-substituted morpholine in admixture with water whereby the water content of the solvent for the liquid-liquid extraction amounts to between 2-15 weight percent and for the extractive distillation amounts to between 0 and 8 weight percent.

14 Claims, 1 Drawing Figure

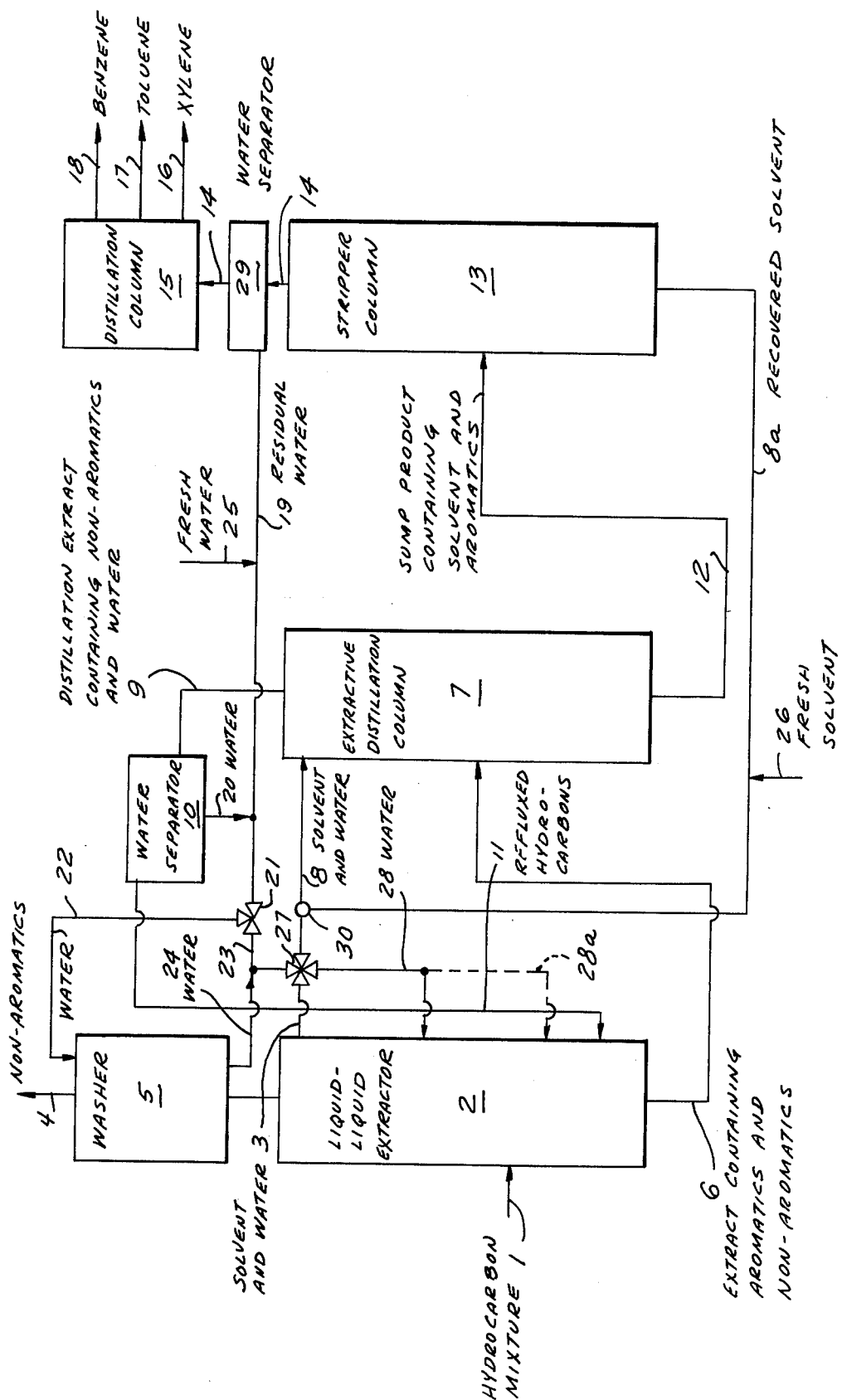

PROCESS FOR RECOVERING HIGHLY PURE AROMATICS FROM A MIXTURE OF AROMATICS AND NON-AROMATICS

CROSS-REFERENCE TO RELATED APPLICATIONS

This application is a continuation of application Ser. No. 526,367 filed Nov. 22, 1974, which in turn was a successive continuation of applications No. 432,341, filed Jan. 10, 1974, and Ser. No. 170,900, filed Aug. 11, 1971 all of these three applications have been abandoned.

The instant invention relates to a process for recovering highly pure aromatic substances from hydrocarbon mixtures which contain in addition to the aromatic substances large amounts of non-aromatic substances by liquid-liquid extraction in combination with an after arranged extractive distillation.

In recent years, there have been more and more frequently used for separating aromatic substances from hydrocarbon mixtures containing the same extractive distillation processes. This type of procedure has in contrast to the liquid-liquid extraction procedures known for a longer time for the same purpose, a considerable number of advantages. As examples of such advantages there may be mentioned the simplification of the apparatus for recovering the selective solvent from the raffinate, the elimination of extensive mechanical installation as for instance, the requirement for a large amount of circulating and other movable components. Furthermore, because of the higher temperatures used in the extractive distillation, the viscosity of the selective solvent which is used therein is markedly decreased with the result that the exchange between the solvent and the substance to be extracted is essentially improved. As a result there is realized a better loading capacity and this is obtained utilizing smaller amounts of extraction agent and installations of considerably reduced size and complexity. In practice the extractive distillation procedure is utilized where relatively close cuts or fractions having high contents of aromatic substances are required to be worked up and if the product is required to be recovered in a high degree of purity. The ability to recover fractions of a high degree of purity and particularly aromatic fractions of the type herein involved has achieved considerable importance in the last few years as the chemical industry has stepped up their demands in this regard.

The method of carrying out the extractive distillation in which the non-aromatic components in the starting hydrocarbon mixture are to be distilled off at the head of the extractive distillation column is unfortunately associated with the disadvantage that the efficiency of the process is very dependent on the composition of the starting hydrocarbon mixture. The larger the amount of non-aromatic substances present in the starting hydrocarbon mixture the more heat energy must be supplied for driving off this component from the extractive distillation column. There is realized an unequivocal improvement in efficiency of the extractive distillation as compared to the liquid-liquid extraction only when the non-aromatic component in the starting hydrocarbon mixture amounts to less than about 50 weight percent. On the other hand, it is not possible when using liquid-liquid extraction to obtain the high degree of purity of the recovered aromatic substances as are obtained when using extractive distillation techniques. In order to obtain the same results, it is necessary to use in the liquid-liquid extraction, extractors provided with the highest possible number of exchange states which in turn involves that there be used extractors provided for example with rotating or pulsating parts. This latter type of extractor is however very expensive to purchase, requires the expenditure of large sums for maintenance and for energy and in operation is subject to a large number of disturbances interfering with the operation thereof.

It has already been proposed that there be used for recovering aromatic substances from hydrocarbon mixtures containing the same, a combination of a liquid-liquid extraction and an extractive distillation. Thereby using one process it is made possible to operate the liquid-liquid extraction with such small amounts of solvent that only a portion of the aromatic substances present in the starting hydrocarbon mixture are taken up by the solvent. The raffinate phase separated from the liquid-liquid extraction is then subjected to an extractive distillation using the same solvent. The sump product collected from the extractive distillation can then be combined with the aromatic substances recovered from the extract of the liquid-liquid extraction and the combined substances then introduced into a column where the solvent can be separated off. This type of operation, however, has the considerable disadvantage that the total non-aromatic substances present in the starting hydrocarbon mixture must be driven off in an after arranged extractive distillation column under the introduction of considerable amounts of heat.

A further possibility for operation utilizing both liquid-liquid extraction and extractive distillation procedures has been proposed in which in the first stage a substantially completely aromatics-free raffinate is separated off from the hydrocarbon mixture while the extract contains the total of the aromatic substances and a portion of the non-aromatic substances. This extract is then further separated in an after arranged extractive distillation. The sump product which is recovered contains in addition to the solvent the greater part of the aromatic substances present in the starting hydrocarbon mixture while the head product consists of non-aromatic substances and a reduced amount of aromatics. The head product is then introduced into a liquid-liquid extraction.

This last described method of working provides in principle an acceptable way for avoiding the aforenoted disadvantages which are associated with the separately carried out liquid-liquid extraction and extractive distillation procedures. Nevertheless, this last described process has not proved entirely satisfactory. This is due to the fact that up until now a selective solvent has not been found which is equally suitable for use in the liquid-liquid extraction and in the extractive distillation. It is known that entirely different requirements are made of a solvent which is intended for use in a liquid-liquid extraction than one which is intended for use in an extractive distillation. Thus, for instance while in a liquid-liquid extraction there is required to be formed two readily separable liquid phases, in an extractive distillation, the formation of two liquid immiscible phases is to be avoided as much as possible. The miscibility or solubility of the selective solvent is required to be essentially greater in the extractive distillation than in the liquid-liquid extraction.

In order to obtain satisfactory results in the last-described procedure, there must be used in both extraction stages different solvents. This has the disadvantage that naturally there are required additional outlays for apparatus as it is necessary that separate solvent circulations be provided for each of the extraction stages. The use of a single solvent for carrying out both of the extraction stages results in the realization of very little economic advantages, however, in that in only one of the two extraction stages are satisfactory results realized.

It is an object of the instant invention to avoid the foregoing disadvantages and to provide a process for recovering highly pure aromatic instances from mixtures of hydrocarbons containing the same and additionally containing large amounts of non-aromatic substances.

It is another object of this invention to avoid the disadvantages of the known processes by providing for the use of a selective solvent which is equally suitable in both liquid-liquid extraction and extractive distillation.

These and other objects and advantages of the invention will become apparent from a consideration of the following disclosure.

In accordance with the invention there is now provided a process for recovering highly pure aromatic substances from mixtures of hydrocarbons which contain the aromatic substances and additionally a large amount of non-aromatic substances by liquid-liquid extraction in combination with an after arranged extractive distillation whereby the liquid-liquid extraction of the starting hydrocarbon mixture is carried out under conditions whereby the resulting extract contains substantially all of the aromatic substances present in the starting hydrocarbon mixture as well as a portion of the non-aromatic substances, introducing this extract into an after arranged extractive distillation, drawing off the sump product (extract phase) and introducing the same into an after arranged distillation column where it is separated into an aromatic and a solvent fraction while the head product formed in the extractive distillation (raffinate phase) is reintroduced into the bottom part of the extractor for liquid-liquid extraction thereof, wherein there is used in both extractions as selective solvent morpholine and/or N-substituted morpholine in admixture with water, the water content of the solvent for the liquid-liquid extraction amounting to between 2 and 15 weight percent and for the extractive distillation amounting to between 0 and 8 weight percent.

The process of the invention avoids the aforementioned difficulties and disadvantages in that in both extraction stages the same selective solvent is used but having different water contents. The water content in the solvent is very easily established. The selective solvent which is obtained from the after-arranged separating column and which has been freed therein of its content of aromatic substances has in accordance with the instant process generally a water content of 0-8 weight percent so that a portion of this stream of solvent can be introduced directly into the head of the extractive distillation column. The remaining portion of this solvent stream is fed back into the liquid-liquid extraction extractor after addition thereto of sufficient amounts of water as are required to bring the same up to the desired concentration. This addition of the water can be carried out either by introducing the water in the required amount into the solvent fraction and supplying the resulting mixture to the liquid-liquid extraction or by supplying the necessary amount of water separately from the solvent at any desired inlet point in the extractor. It is also possible for the required amount of water to be introduced in divided portions into the extractor at different inlet points in the extractor. The water thusly introduced into the circulation remains therein until a portion thereof is collected with the non-aromatic substances at the head of the extractive distillation column and a portion collected as head product from the separating distillation column. The water can be separated from the hydrocarbons admixed therewith and reintroduced into the liquid-liquid extraction extractor. Advantageously, this water can be used prior to its reintroduction into the liquid-liquid extraction extractor for washing out any residual solvent remaining in the raffinate phase of the liquid-liquid extraction.

The process of the invention is advantageously used when the starting hydrocarbon mixture contains in addition to a relatively high content of non-aromatic substances additionally mixtures of aromatic substances such as for instance benzene, toluene and xylene. There is not required in accordance with the invention that there be used complicated extractors having a large number of stages in order to carry out the liquid-liquid extraction. However, the process of the invention has the result that in the liquid-liquid extraction a quantitative transfer of the aromatic substances present in the starting hydrocarbon into the extract is accomplished. The non-aromatic fraction which is also carried over into the extract is easily separated off therefrom in the after arranged extractive distillation. For carrying out the liquid-liquid extraction, there can be used simply constructed extractors provided with stationary inserts as for instance, perforated plate columns having fixed plates therein. It has been established that, as compared to the previous installations, by using a solvent-water mixture in accordance with the invention no noticeable corrosion of the apparatus is observed. In comparative experiments carried out by the applicants, there was not observed when using an apparatus manufactured of normal steel and when operating continuously and in accordance with the invention, in any case, any decrease in the pH value and a material wearing away of over 0.1 g/hr.m$^2$ only was determined.

The extractive distillation in accordance with the invention was carried out without any external reflux. If the hydrocarbons to be separated have in part very low boiling temperatures, then the process in accordance with the invention can be carried out using instead of normal pressure increased pressure. In certain cases, it has also been found advantageous to carry out the process under vacuum whereby the sump temperature of the extractive distillation column is reduced. This has been found to be particularly advantageous when the starting hydrocarbon mixture contains polymerization forming substances and in particular olefins.

For carrying out the process of the invention it has been found to be particularly advantageous to use N-substituted morpholines, the substituents of which do not contain more than 7 carbon atoms.

The invention will be further illustrated and disclosed by reference to the drawing which is a flow diagram of a preferred embodiment of the process of the invention.

The starting hydrocarbon mixture was introduced via a conduit 1 into the extractor 2 which is constructed as a conventional perforated plate column provided with stationary plates. In extractor 2, the starting hydrocarbon mixture is subjected to liquid-liquid extraction, the solvent-water mixture for the extraction being introduced over conduit 3 into the extractor 2. The non-aromatic substances (raffinate phase) are drawn off from the head of the extractor 2 through conduit 4. Advantageously, there can be arranged in the vicinity of conduit 4 the washer 5 where the raffinate phase can be washed free of any solvent carried along therewith. The total aromatic substances and a portion of the non-aromatic substances constituting the extract are drawn off from the extractor 2 through conduit 6 and delivered into the mid portion of the extractive distillation column 7. There is introduced through conduit 8 for use in carrying out the extractive distillation, solvent-water mixture at the level of one of the top-most plates of the extractive distillation column 7. The head product taken off from the extractive distillation consists of non-aromatic substances and water and also a small amount of aromatic substances. This head product is taken off through conduit 9 and introduced into water separator 10. The water phase is separated off from the hydrocarbons in the separator. The hydrocarbons are then reintroduced over conduit 11 into the bottom portion of the extractor 2. The sump product of the extractive distillation which in the main consists of aromatic substances, solvent and a small amount of water is taken off from the extractive distillation column 7 through conduit 12 and introduced into the distillation column 13. The recovered solvent can be taken off from the sump of the distillation column 13 through conduit 8a. It usually contains after distillation only such an amount of water that it can be directly introduced through conduit 8 into the extractive distillation column 7. The portion of the solvent required for use in the liquid-liquid extraction is branched off at 30 into conduit 3. The head product of the distillation 13 contains the total amount of aromatic substances as well as small amounts of residual water. This head product is then fed into column 15 in which the head product is further separated into its component parts. The conduits 16, 17 and 18 serve for the taking off of benzene, toluene and xylene. The residual water separated in the water separator 29 is taken off by a conduit 19 and combined with the water flowing through conduit 20 and which has come from water separator 10. This water is reused for admixture with the solvent to be used in extractor 2. In this connection there are present a number of possibilities.

First the water can at the vicinity of the valves 21 and 27 be delivered over conduit 23 into conduit 3 where it is mixed with solvent before the introduction thereof into extractor 2.

The valve 27, however, can be so arranged that the water from the conduit 19 via conduit 23 is directly introduced into the conduit 28 and through this conduit separate and apart from the solvent introduced into the extractor 2 at a selected entry point. The conduit 28a shown by broken lines indicates the possibility whereby the water stream flowing through the conduit 28 can be broken down into further separate streams and these individually introduced at different points of the reactor. Thereby a gradation in the selectivity of the solvent-water in the separating stages of the extractor can be realized.

Finally, the valve 21 can be so installed that the water from conduit 19 is first introduced into conduit 22 and from there supplied to the washer 5 where it is used to wash out any residual solvent remaining in the raffinate phase of the liquid-liquid extraction. The water flowing out of the washer 5 is then delivered over conduit 24 into conduit 23 to the valve 27. Thereafter, depending on the valve's position, it flows from there into the conduit 3 or 28.

Additional water can be introduced through conduit 25 as required for making up any water losses which have occurred. Additional solvent can be introduced through conduit 26 for making up any losses of solvent in the circulation.

The practical operation of the process of the invention can be seen from the following example. As starting material a hydrocarbon mixture was used constituting a reformate fraction containing benzene and toluene. As selective solvent N-formyl morpholine was used in both stages. In the following Table 1, the important analysis data are set out in weight percent. The reference numerals used therein refer to the reference numerals used in the flow diagram.

TABLE 1

| Substance | conduit 1 | raffinate conduit 4 | head product conduit 9 | pure benzene conduit 16 | pure toluene conduit 17 |
|---|---|---|---|---|---|
| $C_4$-hydrocarbons | 0.06 | 0.08 | 0.02 | | |
| $C_5$-hydrocarbons | 10.3 | 15.4 | 10.8 | | |
| $C_6$-hydrocarbons | 25.3 | 40.7 | 37.8 | 0.022 | |
| $C_7$-hydrocarbons | 19.4 | 30.2 | 28.7 | | |
| $C_8$-hydrocarbons | 6.3 | 12.4 | 8.4 | | 0.008 |
| $C_9$-hydrocarbons | 0.2 | 0.3 | 0.5 | | |
| benzene | 7.8 | 0.028 | 9.0 | 99.978 | |
| toluene | 30.7 | 0.85 | 4.8 | | 99.992 | yield purest benzene = 99.77 %
yield purest toluene = 98.32 %

In carrying out the process, the following temperatures were used:

| | |
|---|---|
| extractor 2 | 60° C |
| extractive distillation: | |
| delivery from conduit 8 | 80° C |
| delivery from conduit 6 | 98° C |
| sump | 174° C |
| distillation column 13: | |
| delivery from conduit 12 | 174° C |
| heat product from | |
| conduit 14 | 88° C |
| sump | 160° C |

In the foregoing instances the following amounts were introduced:

| | |
|---|---|
| starting hydrocarbon mixture from conduit 1 | 295 kg |
| solvent with 2.5 wt.-% $H_2O$ from conduit 3 | 858 kg |
| water from conduit 28 = solvent with 5.6 wt.-% $H_2O$ | 27 kg / 885 kg |
| raffinate from conduit 4 | 179 kg |
| extract from conduit 6 | 1047 kg |
| solvent with 2.5 wt.-% $H_2O$ from conduit 8 | 144 kg |

-continued

| | |
|---|---|
| head product from conduit 9 | 51 kg |
| water from conduit 20 | 1 kg |
| sump product from conduit 12 | 996 kg |
| pure aromatic substances from conduit 14 | 111 kg |
| water from conduit 19 | 26 kg |

The results of this Example in accordance with the process of the invention established that with the said process, it is possible to obtain aromatic substances in very high yields having very high degrees of purity.

Without further analysis, the foregoing will so fully reveal the gist of the present invention that others can by applying current knowledge readily adapt it for various applications without omitting features that, from the standpoint of prior art, fairly constitute essential features of the generic or specific aspects of this invention and, therefore, such adaptations should and are intended to be comprehended within the meaning and range of equivalence of the following claims.

What is claimed as new and desired to be secured by Letters Patent is set forth in the appended claims:

1. The process of recovering the aromatics from a feed containing a mixture of aromatic and non-aromatic hydrocarbons comprising the steps of
    introducing the said feed into a liquid-liquid extractor column while introducing solvent and water into the top section of said column above the level of introduction of said feed, withdrawing non-aromatics as raffinate and withdrawing aromatics and solvent-water together with a minor amount of non-aromatics as the extract;
    passing the said extract at about midpoint into an extractive distillation column which is operated so as to have both a rectifying section and a stripping section while passing solvent or a solvent-water mixture into the top section of the column, withdrawing the head product essentially consisting of non-aromatic hydrocarbons from said column and refluxing it into the lower section of the liquid-liquid extractor and withdrawing the bottom product consisting essentially of aromatics and a solvent-water mixture and
    finally passing the latter bottom product into a distillation column so as to separate the aromatics and a part of the water as head product from a solvent-water mixture as bottom product, recovering the aromatics and recycling the solvent-water mixture; the solvent in steps and being the same and the amount of water in the solvent-water mixture passed into or formed in said liquid-liquid extractor being in excess of the corresponding water in said extractive distillation column whereby formation of a two-phase liquid system in the liquid-liquid extractor is promoted while the capacity of the solvent for the non-aromatics in said extractive distillation step is decreased.

2. The process of claim 1 wherein the solvent-water mixture separated from the aromatics in said final distillation step is recycled in part into the extractive distillation column and in part into the liquid-liquid extractor column, the excess water in said latter column being obtained by introducing water into said liquid-liquid extractor in addition to the water in said recycled solvent-water mixture.

3. The process of claim 2 wherein water is separated from the head products both of the extractive distillation column and of the final distillation column and is recycled into the liquid-liquid extractor to form said excess amounts of water in the latter column.

4. The process of claim 3 wherein all or part of the said recycled water is first employed to wash residual solvent out of the raffinate withdrawn from the liquid-liquid extractor column before passed into the latter column.

5. The process of claim 2 wherein all or part of said additional water is mixed with the portion of the solvent-water mixture recycled into the liquid-liquid extractor column prior to its introduction into the column.

6. The process of claim 2 wherein provision is made to introduce additional solvent from an external source into the recycled solvent-water mixture to make up solvent losses occurring during the operation.

7. The process of claim 2 wherein provision is made to add further water from an external source to said additional water to make up losses occurring during the operation.

8. The process of claim 1 wherein the solvent is morpholine or N-substituted morpholine.

9. The process of claim 8 wherein the solvent is N-formyl morpholine.

10. The process of claim 1 wherein the water contents in the water-solvent mixture introduced into the top section of the extractive distillation column is at most 8% by weight and the water contents in the total of solvent-water mixture introduced into or formed in the top section of the liquid-liquid extractor is between 2 and 15% by weight.

11. The process of claim 1 wherein the liquid-liquid extraction is effected in an extractor having stationary perforated plates.

12. The process of claim 1 wherein the aromatics withdrawn as the head product of the final distillation column are separated into their individual components prior to final recovery.

13. The process of claim 1 wherein the extractive distillation is carried out under pressure.

14. The process of claim 1 wherein the extractive distillation is carried out in a vacuum.

* * * * *